United States Patent [19]
Tuszko et al.

[11] Patent Number: 5,269,949
[45] Date of Patent: Dec. 14, 1993

[54] MODIFIED ANTI-SUCTION CYCLONE SEPARATION METHOD AND APPARATUS

[76] Inventors: Wlodzimierz J. Tuszko, 5434 Camino De Ville, Camarillo, Calif. 93012; Wojciech J. Tuszko, 918 4th St., #2, Santa Monica, Calif. 90403

[21] Appl. No.: 944,068

[22] Filed: Sep. 11, 1992

[51] Int. Cl.⁵ .................. B01D 21/26; B04C 1/00
[52] U.S. Cl. .................. 210/788; 210/787; 210/512.1; 209/144; 209/211; 73/23.41
[58] Field of Search .......... 210/295, 512.1, 787, 210/788; 209/144, 211; 55/459.1, 97; 73/23.41

[56] References Cited

U.S. PATENT DOCUMENTS

| | | | |
|---|---|---|---|
| 4,737,271 | 4/1988 | Childs | 209/211 |
| 4,738,147 | 4/1988 | Tomlin | 55/97 |
| 4,927,298 | 5/1990 | Tuszko et al. | 209/211 |
| 5,071,542 | 12/1991 | Tuszko et al. | 55/459.1 |
| 5,080,697 | 1/1992 | Finke | 55/97 |

*Primary Examiner*—Robert A. Dawson
*Assistant Examiner*—David Reifsnyder
*Attorney, Agent, or Firm*—Fulwider, Patton, Lee & Utecht

[57] ABSTRACT

The modified anti-suction air cyclone method and apparatus insulate the air core base as a most suction active part of the air core to prevent separated particles from being entrained from the cyclone walls into the inner vortex. Use of the air core bed can greatly increase separation efficiency and capacity of a given cyclone dust collector and decrease the investment and maintenance costs.

2 Claims, 2 Drawing Sheets

MODIFIED ANTI-SUCTION CYCLONE SEPARATION METHOD AND APPARATUS

FIELD OF INVENTION

This invention relates to a method and apparatus for centrifugally separating or collecting solid particles of foreign matter from a fluid. More specifically the invention is directed to improving separation efficiency of a cyclone dust collector, to increase its capacity, and to reduce investment and maintenance costs of such a cyclone dust collector.

BACKGROUND

As early cyclone method and apparatus is known from U.S. Pat. No. 453,105 (Bretney), issued May 26, 1891, in which there are two stages, in line, in the separating cyclone. A frequent problem with this and later cyclone devices is that efficiency of separation is markedly decreased after either capacity or feed solids concentration are increased. Later cyclone designs eliminated the small in-line second stage cyclone, but introduced only slight construction changes, not changing, however, the general principle of cyclone operation and not eliminating those disadvantages.

A cyclone is a device for a creation of a vortex and it is the vortex that does the work in separating the particulate matter from the gas. In all presently used air cyclone devices this vortex can enter the discharge dust bin to cause an excessive upflow of settled particles. To decrease a harmful effect of this suction, an anti-suction discharge valve or other similar expensive devices are required, but in spite of such devices the separation efficiency is reduced.

The new features of the cyclone air core was discovered and afterwards used to greatly improve the cyclone collector (Wlodzimierz J. Tuszko et al: U.S. Pat. No. 4,927,298 issued May 22, 1990, U.S. Pat. No. 5,071,542 issued Dec. 10, 1991, Ser. No. 07/807443 filed Dec. 13, 1991)

It is therefore one object of the present invention to reduce the particulate matter emission in clean gas to 0.2 compared to the conventional cyclone.

A further object of the present invention is to reduce the harmful negative pressure in hopper to 0.25 in the vacuum fed cyclone and to 0 in pressure fed cyclone.

Still another object of the present invention is to increase 1.3 fold the feed capacity of the cyclone.

Still another object of the present invention is to increase 2.0 fold the operational life both of the cyclone and the hopper compared to the conventional ones.

The last object of the invention is to get an easy means to sample taking of the cyclone clean gas to determine the amount of particulate matter in it.

SUMMARY OF THE INVENTION

This invention relates to a device for separation of particulate fluid suspensions known as a cyclone, in which centrifugal forces of the revolving particulate suspension cause separation of the suspensions into finer and coarser or light and denser fractions. There are two kinds of air cyclones—pressure cyclones having a blower connected with a cyclone inlet pipe, and vacuum cyclones having a blower connected with a cyclone overflow pipe. Separation efficiency of such conventional cyclone dust collectors is considerably reduced because the separated particles are entrained by suction of the vortex air core in its lower part. To avoid the phenomenon, the present invention provides insulating the vortex air core base to prevent the suction and to ensure a high and steady separation efficiency. For a pressure fed cyclone the presence of the air core bed makes it possible to obtain a positive air pressure in the discharge dust bin. For a vacuum cyclone, it makes it possible to greatly reduce a negative air pressure in the discharge bin.

To take advantage from newly discovered features of the air core base, the invention introduces an easy way to take the samples of cyclone clean gas to determine the amount of particulate matter in it.

DETAILED DESCRIPTION OF THE INVENTION

Figure 1:
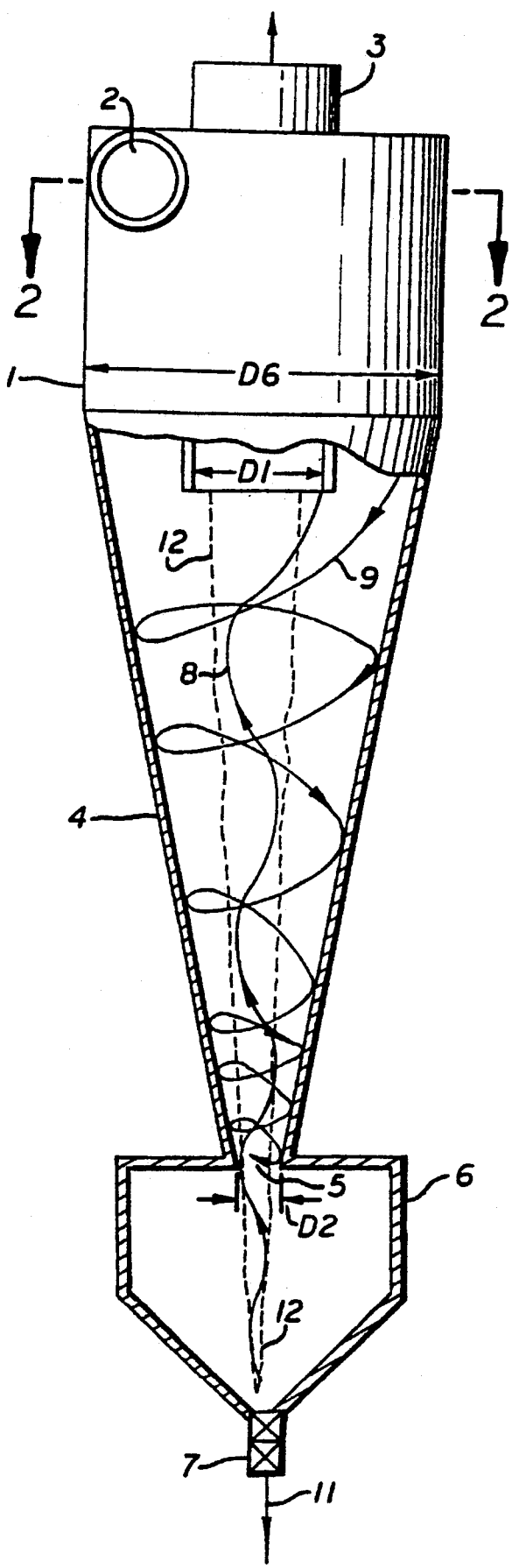
FIG. 1 is a cross-sectional elevational view of a regular cyclone dust collector.
Figure 2:
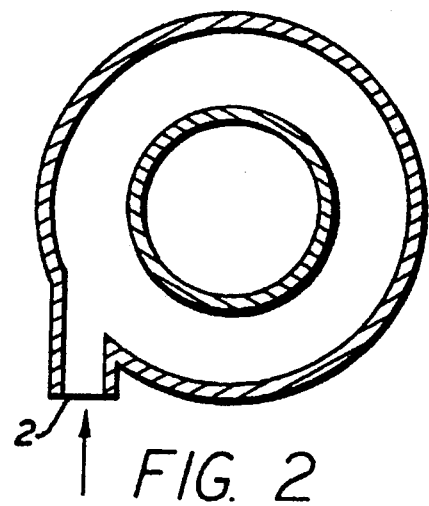
FIG. 2 is a cross-sectional view of the regular cyclone dust collector taken along line 02-2 of FIG. 1.

A regular cyclone dust collector for centrifugally separating or collecting said particles of foreign matter from a fluid is illustrated in FIG. 1 and FIG. 2. This cyclone is comprised of a cylindrical portion 1 having an inlet duct 2 for introduction of a feed suspension in a tangential direction. An exhaust or pipe 3 extends through the top or ceiling wall of the cylindrical portion. 1. A frustoconical portion 4 extends below the straight cylindrical portion 1. An outlet 5 for separating heavier or coarser product at the bottom of the frustoconical portion 4 is axially aligned with the overflow exhaust pipe 3. A dust bin or hopper 6 extends below the outlet 5 of frusto-conical portion 4 and it is equipped with an anti-suction dust discharge valve 7 or another device like for example a suction blower. The dust bin 6 and valve 7 are axially aligned with the overflow exhaust pipe 3. In the portions 1 and 4 together, as in the separating chamber, the feed suspension flows in a helical swirling flow pattern so as to establish counterflowing inner 8 and outer 9 vortexes within the separating chamber, inherently causing solids in the fluid flow, which are small or lighter to move in the inner vortex 8 and exit through the overflow exhaust pipe 3 as a smaller or lighter product stream or overflow 10. Ingredients in the fluid flow which are coarser or heavier moved to the outer vortex 9 and exit the cyclone on the walls of the cyclone through the outlet 5 as a coarser or heavier solid product stream or as an underflow 11. All of the air entering inlet duct 2, after the separating work is done, gets to inner vortex 8 to leave the cyclone through overflow exhaust pipe 3. A separation efficiency of every regular cyclone dust collector is considerably reduced because the separated particles are entrained from the cyclone walls by suction of vortex air core 12 along its lower part especially when dust discharge valve 7 is opened.

Figure 3:
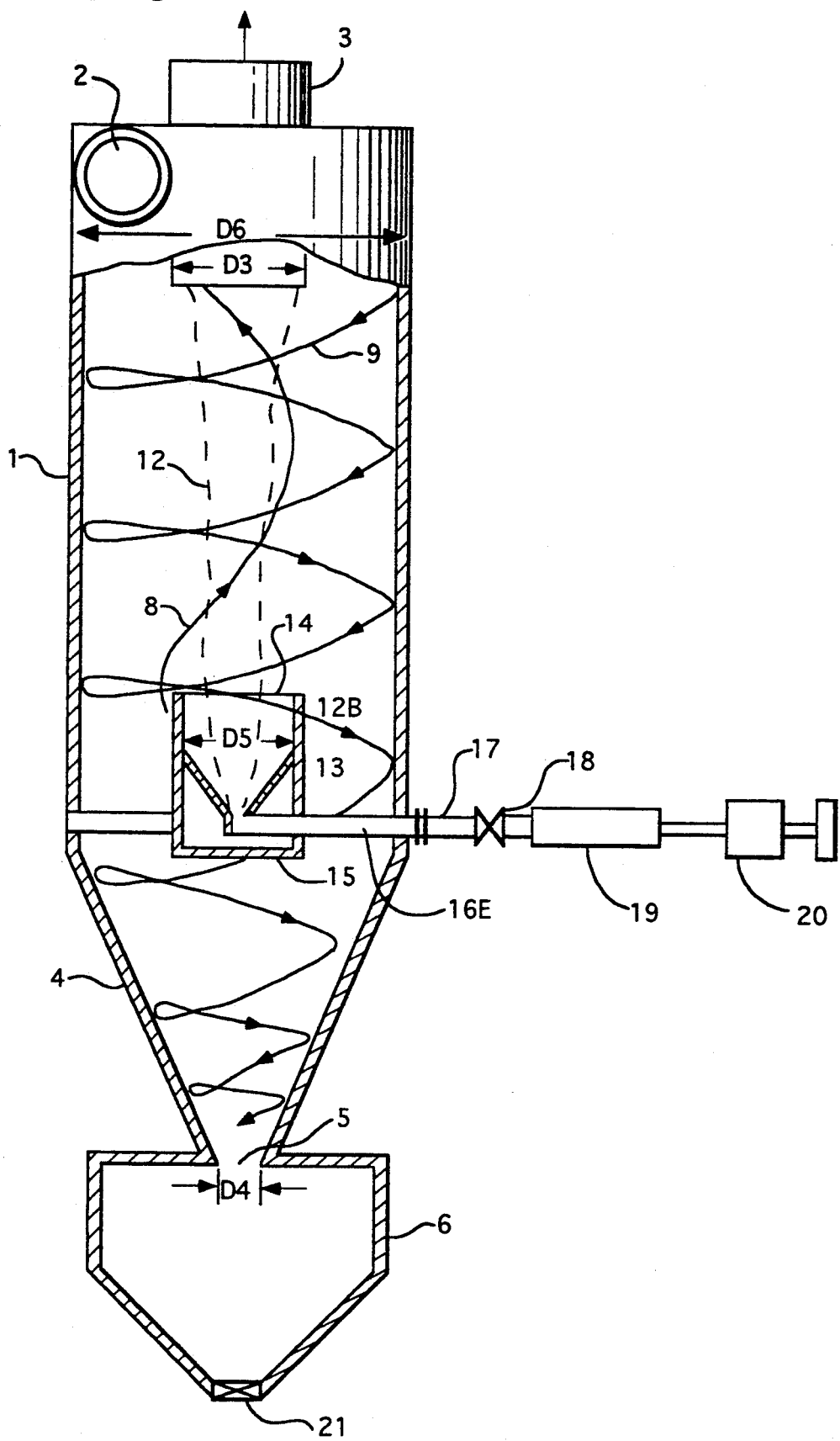
FIG. 3 is a partial sectional elevational view of the modified no suction air cyclone.

The modified no-suction air cyclone method and apparatus for separating or collecting solid particles of foreign matters from a fluid is illustrated in FIG. 3. In the invented method, only the cyclone air core 12 base 12B is caught into an artificial bed or channel 13 to be insulated from neighboring underlying layers to the inner vortex 8. Then the separated solid particles not being disturbed can get to the discharge device. Then in the pressure fed cyclone not all of the air entering inlet duct 2 can leave the cyclone through the overflow exhaust pipe 3 and a part of the air leaves the cyclone through the underflow outlet 5 to get into dust hopper 6 and to eliminate negative pressure in it. This artificial bed or channel 13 of metal, wood, or plastic is opened on its top 14 to introduce the air core 12 in it and is closed on its bottom 15. The air core bed 13 extends coaxially only in the lowest part of the cyclone cylindrical portion, in order to permit undisturbed downward movement of solid particulate matter in the frustoconical portion of the cyclone. The air core bed 13 is radially attached to the walls of the cyclone by means of the rigid elements 16. One or more of these elements 16 is empty inside 16E and it serves to connect the bottom 15 of air core bed 13 through the pipe 17 equipped with valve 18 and throughout an air filtration system 19 to a source of negative pressure 20. The bottom 15 of the air core bed 13 provides an area from which samples can be taken, which are representative of particulate emissions in cleaned gas produced by the cyclone. The elements 16E, 17, 18, 19, and 20 are used for taking samples of particulate matter from within the cyclone. On the bottom of the dust hopper 6 a regular dust discharge valve 21 is attached. The cross sectional area D3 of the modified no-suction air cyclone (MNSAC) overflow exhaust pipe 3, shown in the FIG. 3 can be the same as D1 of a regular cyclone shown on FIG. 1. The cross sectional area D4 of MNSAC outlet 5 can be the same as D2 of a regular cyclone shown in FIG. 1. The cross sectional area D5 of air core bed 13 can be similar, the same, or bigger than the cross sectional area D3 of the overflow exhaust pipe 3 so that the intake of a gas sample can be drawn from the largest part of the inner vortex, preferably from the entire cross-sectional area D3 of the overflow exhaust pipe, and so that the horizontal bottom cover of the air core bed can insulate the underlying layers of the inner vortex, at least to the same extent as the cross-sectional area D4 of the underflow outlet 5.

The modified no-suction air cyclone of 9" diameter was built and tested qualitatively and quantitatively. The test proved that MNSAC allows users to reduce the particulate matter emission in clean gas to 0.2; to reduce the harmful negative pressure in hopper to 0.25 in vacuum fed cyclone or to 0 in pressure fed cyclone; to increase 1.3 fold the fed capacity; to increase 2.0 fold operational life both the cyclone and the hopper, all of these compared to conventional cyclone. In addition, the MNSAC gives the users the simplest method of sample taking of the cyclone clean gas to determine the particulate matter in it.

This invention is not to be limited by the embodiments shown in the drawings or described in the description, which is given by way of example and not limitation, but only in accordance with the scope of the appended claims.

I claim:

1. In a method for separating solid particles of foreign matter from a feed gas delivered in a fluid flow to a cyclone having walls forming an axially elongated cylindrical-conical separating chamber having a conical bottom portion with a bottom outlet, a dust hopper connected to said bottom outlet of said conical portion, a cylindrical upper portion with an exhaust pipe in communication with the cylindrical upper portion of said separating chamber, and an inlet duct in said cylindrical upper portion for introducing said feed gas into said cylindrical upper portion in a tangential direction in a helical swirling flow pattern so as to establish within the separating chamber counterflowing inner and outer vortexes, causing a lighter portion of said particles in said feed gas to move to the inner vortex and to exit through said exhaust pipe as overflow, and a heavier portion of said particles to move to the outer vortex and to exit through the bottom outlet as underflow, the method including the step of forming a cyclone air core having a base in the cyclone, the improvement of said method comprising the steps of:

insulating only the cyclone air core base from underlying neighboring portions to the inner vortex so that the particles cannot be pulled into the inner vortex, by disposing an air core bed duct having a closed lower end to extend coaxially only in the lowest cylindrical portions of the cyclone to improve separation efficiency and feed capacity as well as to reduce a negative pressure in the dust hopper, the air core having an air core bed with a cross-sectional area larger than the cross-sectional area of the underflow outlet, whereby said air core bed insulates the underlying feed gas layers in the conical bottom portion; and introducing the air core base to withdraw samples of cleaned gas in the cyclone by means of a valved pipe connection.

2. In a cyclone dust collector apparatus having walls forming an axially elongated cylindrical-conical separating chamber, said chamber having an upper cylindrical portion and a lower conical portion, said lower conical portion having an bottom outlet for an underflow product stream through an underflow exhaust, said upper cylindrical portion having an overflow exhaust pipe having an inlet duct in said cylindrical portion for introducing a feed gas into said cylindrical portion in a tangential direction, said lower conical portion having a dust hopper connected to said bottom outlet, the improvement comprising:

an air core bed duct for an air core in the cyclone, the air core bed duct having a closed lower end extending coaxially only in the lowest cylindrical portion of the cyclone for insulating only the air core base from underlying neighboring portions of feed gas, to prevent solid particles from being pulled into an inner vortex, and to increase cyclone capacity and efficiency, the cross-sectional area of the air core bed being larger than the cross-sectional area of the underflow outlet; and the air core bed having a bottom portion for withdrawing samples of gas cleaned by the cyclone by means of a valved pipe connection.

* * * * *